United States Patent
Popovic

(10) Patent No.: US 9,615,886 B2
(45) Date of Patent: Apr. 11, 2017

(54) ROBOTIC CONTROL OF AN ENDOSCOPE FROM BLOOD VESSEL TREE IMAGES

(75) Inventor: Aleksandra Popovic, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 520 days.

(21) Appl. No.: 13/822,001

(22) PCT Filed: Sep. 13, 2011

(86) PCT No.: PCT/IB2011/053998
§ 371 (c)(1),
(2), (4) Date: Mar. 11, 2013

(87) PCT Pub. No.: WO2012/035492
PCT Pub. Date: Mar. 22, 2012

(65) Prior Publication Data
US 2013/0165948 A1   Jun. 27, 2013

Related U.S. Application Data

(60) Provisional application No. 61/382,980, filed on Sep. 15, 2010.

(51) Int. Cl.
A61B 1/00 (2006.01)
A61B 1/04 (2006.01)
(Continued)

(52) U.S. Cl.
CPC ........... *A61B 19/50* (2013.01); *A61B 1/0005* (2013.01); *A61B 1/3137* (2013.01); *A61B 34/30* (2016.02);
(Continued)

(58) Field of Classification Search
CPC ........... A61B 19/2203; A61B 19/2211; A61B 19/5244; A61B 19/5246; A61B 19/5251;
(Continued)

(56) References Cited

U.S. PATENT DOCUMENTS

| | | | |
|---|---|---|---|
| 7,233,820 B2 * | 6/2007 | Gilboa | 600/427 |
| 2007/0001879 A1 | 1/2007 | Kaftan et al. | |

(Continued)

FOREIGN PATENT DOCUMENTS

| | | |
|---|---|---|
| FR | 2855292 | 11/2004 |
| JP | 2002017752 A | 1/2002 |
| WO | 2009117989 A2 | 10/2009 |

OTHER PUBLICATIONS

C. Gnahm et al., "Towards Navigation on the Heart Surface During Coronary Artery Bypass Grafting", Ing. J. CARS (2009) 5:105-112.

(Continued)

*Primary Examiner* — Anhtuan T Nguyen
*Assistant Examiner* — William Chou

(57) ABSTRACT

A robot guiding system employs a robot unit (10) and a control unit (20). The robot unit (10) includes an endoscope (12) for generating an intra-operative endoscopic image (14) of a blood vessel tree within an anatomical region, and a robot (11) for moving the endoscope (12) within the anatomical region. The control unit (20) includes an endoscope controller (22) for generating an endoscopic path within the anatomical region, wherein the endoscopic path is derived from a matching of a graphical representation of the intra-operative endoscopic image (14) of the blood vessel tree to a graphical representation of a pre-operative three-dimensional image (44) of the blood vessel tree. The control unit (20) further includes a robot controller (21) for commanding the robot (11) to move the endoscope (12) within the anatomical region in accordance with the endoscopic path.

12 Claims, 5 Drawing Sheets

(51) Int. Cl.
*A61B 1/06* (2006.01)
*A61B 19/00* (2006.01)
*A61B 1/313* (2006.01)
*G06T 7/00* (2017.01)
*A61B 17/00* (2006.01)
*A61B 90/00* (2016.01)
*A61B 34/30* (2016.01)

(52) U.S. Cl.
CPC .......... *G06T 7/0032* (2013.01); *G06T 7/0046* (2013.01); *A61B 1/0016* (2013.01); *A61B 1/00149* (2013.01); *A61B 2017/00252* (2013.01); *A61B 2034/301* (2016.02); *A61B 2090/364* (2016.02); *A61B 2090/3614* (2016.02); *G06T 2207/10068* (2013.01); *G06T 2207/10072* (2013.01); *G06T 2207/20072* (2013.01); *G06T 2207/30101* (2013.01)

(58) Field of Classification Search
CPC ............ A61B 19/5255; A61B 19/5265; A61B 2019/5289; A61B 2019/5291; A61B 2019/5295
USPC .................. 600/102, 109, 114, 117, 118, 160
See application file for complete search history.

(56) References Cited

U.S. PATENT DOCUMENTS

| | | | |
|---|---|---|---|
| 2007/0147707 A1* | 6/2007 | Coste-Maniere et al. | 382/298 |
| 2007/0167784 A1* | 7/2007 | Shekhar | A61B 6/032 600/443 |
| 2007/0237373 A1 | 10/2007 | Kiraly et al. | |
| 2008/0207997 A1 | 8/2008 | Higgins et al. | |
| 2009/0292171 A1 | 11/2009 | Ito | |
| 2010/0041949 A1* | 2/2010 | Tolkowsky | 600/109 |
| 2011/0028992 A1 | 2/2011 | Geiger et al. | |
| 2011/0105879 A1* | 5/2011 | Masumoto | G06F 19/321 600/407 |
| 2012/0046521 A1* | 2/2012 | Hunter et al. | 600/104 |

OTHER PUBLICATIONS

M.W. Graham et al., "Robust 3-D Airway Tree Segmentation for Image-Guided Peripheral Bronchoscopy", IEEE Transactions on Medical Imaging, col. 29, No. 4, Apr. 2010, pp. 982-997.

W.E. Higgins et al., "3D CT-Video Fusion for Image-Guided Bronchoscopy", NIH Public Access Author Manuscript, pp. 1-31; Published in Final Edited form as: Comput. Med. Imaging Graph. Apr. 2008; 32(2): 159-173.

S.A. Merritt et al., "Image-Guided Bronchoscopy for Peripheral Lung Lesions: A Phantom Study", www.chestjournal.org, Chest 2008; 134; Nov. 5, 2008, pp. 1017-1026.

K. Mori et al., "Automated Anatomical Labeling of Bronchial Branches Extracted from CT Datasets Based on Machine Learning and Combination Optimization and its Application to Bronchoscope Guidance" (Abstract), Medical Image Computing and Computer-Assisted Intervention—MICCAI 2009; Proceedings 12th International Conference.

A. Popovic et al., "An Approach to Robotic Guidance of an Uncalibrated Endoscope in Beating Heart Surgery", Proceedings of the 2010 3rd IEEE RAS & EMBS International Conference on Biomedical Robotics and Biomethatronics, The University of Tokyo, Tokyo, Japan, Sep. 26-29, 2010, pp. 106-113.

E.U. Schirmbeck et al., "Automatic Coronary Artery Detection on in Situ Heart Images", Computers in Cardiology 2004; 31: 785-788.

* cited by examiner

ROBOTIC CONTROL OF AN ENDOSCOPE FROM BLOOD VESSEL TREE IMAGES

The present invention generally relates to robotic control of an endoscope during a minimally invasive surgical procedure (e.g., a minimally invasive coronary bypass grafting surgery). The present invention specifically relates to a matching of a graphical representation of a pre-operative three-dimensional ("3D") blood vessel tree image to a graphical representation of an intra-operative endoscopic blood vessel tree image as a basis for robotic guiding of an endoscope.

Coronary artery bypass grafting ("CABG") is a surgical procedure for revascularization of obstructed coronary arteries. Approximately 500,000 operations are performed annually in the United States. In conventional CABG, the patient's sternum is opened and the patient's heart is fully exposed to a surgeon. Despite the exposure of the heart, some arteries may be partially invisible due to fatty tissue layer above them. For such arteries, the surgeon may palpate the heart surface and feel both blood pulsating from the arteries and a stenosis of the arteries. However, this data is sparse and might not be sufficient to transfer a surgical plan to the surgical site.

In minimally invasive CABG, the aforementioned problem of conventional CABG is amplified because a surgeon cannot palpate the heart surface. Additionally, the length of surgical instruments used in minimally invasive CABG prevents any tactile feedback from the proximal end of the tool.

One known technique for addressing the problems with conventional CABG is to register an intra-operative site with a pre-operative 3D coronary artery tree. Specifically, an optically tracked pointer is used to digitalize position of the arteries in an open heart setting and the position data is registered to pre-operative tree using an Iterative Closest Point ("ICP") algorithm known in art. However, this technique, as with any related approach matching digitized arteries and pre-operative data, is impractical for minimally invasive CABG because of spatial constraints imposed by a small port access. Also, this technique requires most of the arteries to be either visible or palpated by the surgeon, which is impossible in minimally invasive CABG.

One known technique for addressing the problems with minimally invasive CABG is to implement a registration method in which the heart surface is reconstructed using an optically tracked endoscope and matched to pre-operative computer tomography ("CT") data of the same surface. However, this technique, as with any related approach proposing surface based matching, may fail if the endoscope view used to derive the surface is too small. Furthermore, as the heart surface is relatively smooth without specific surface features, the algorithm of this technique more often than not operates in a suboptimal local maximum of the algorithm.

Another known technique for addressing the problems with minimally invasive CABG is to label a coronary tree extracted from a new patient using a database of previously labeled cases and graph based matching. However, this technique works only if a complete tree is available and it's goal is to label the tree rather to match the geometry.

A further problem of minimally invasive CABG is an orientation and a guidance of the endoscope once the global positioning with respect to pre-operative 3D images is reached. The goal of registration is to facilitate localization of the anastomosis site and the stenosis. In a standard setup, the endoscope is being held by an assistant, while the surgeon holds two instruments. The surgeon issues commands to the assistant and the assistant moves the endoscope accordingly. This kind of setup hinders hand-eye coordination of the surgeon, because the assistant needs to intuitively translate surgeon's commands, typically issued in the surgeon's frame of reference, to the assistant's frame of reference and the endoscope's frame of reference. Plurality of coordinate systems may cause various handling errors, prolong the surgery or cause misidentification of the coronary arteries.

A surgical endoscope assistant designed to allow a surgeon to directly control an endoscope via a sensed movement of the surgeon head may solve some of those problems by removing the assistant from the control loop, but the problem of transformation between the surgeon's frame of reference and the endoscope's frame of reference remains.

The present invention provides methods for matching graphical representations of a blood vessel tree (e.g., furcation of arteries, capillaries or veins) as shown in a pre-operative three-dimensional ("3D") image (e.g., a CT image, a cone beam CT image, a 3D X-Ray images or a MRI image) and in an intra-operative endoscopic image, overlaying the blood vessel tree from the pre-operative 3D image to the intra-operative endoscopic image, and using the overlay to guide a robot holding an endoscope toward a location as defined in the pre-operative 3D image.

One form of the present invention is a robotic guiding system employing a robot unit and a control unit.

A robot guiding system employs a robot unit and a control unit. The robot unit includes an endoscope for generating an intra-operative endoscopic image of a blood vessel tree within an anatomical region, and a robot for moving the endoscope within the anatomical region. The control unit includes an endoscope controller for generating an endoscopic path within the anatomical region, wherein the endoscopic path is derived from a matching of a graphical representation of the intra-operative endoscopic image of the blood vessel tree to a graphical representation of a pre-operative three-dimensional image of the blood vessel tree. The control unit further includes a robot controller for commanding the robot to move the endoscope within the anatomical region in accordance with the endoscopic path.

A second form of the present invention is a robot guiding method involving a generation of an intra-operative endoscopic image of a blood vessel tree within an anatomical region and a generation of an endoscopic path within the anatomical region, wherein the endoscopic path is derived from a matching of a graphical representation of the intra-operative endoscopic image of the blood vessel tree to a graphical representation of a pre-operative three-dimensional image of the blood vessel tree. The robot guiding method further involves a commanding of a robot to move an endoscope within the anatomical region in accordance with the endoscopic path.

The term "pre-operative" as used herein is broadly defined to describe any activity executed before, during or after an endoscopic imaging of an anatomical region for purposes of acquiring a three-dimensional image of the anatomical region, and the term "intra-operative" as used herein is broadly defined to describe any activity executed by the robot unit and the control unit during an endoscopic imaging of the anatomical region. Examples of an endoscopic imaging of an anatomical region include, but are not limited to, a CABG, a bronchoscopy, a colonoscopy, a laparascopy, and a brain endoscopy.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
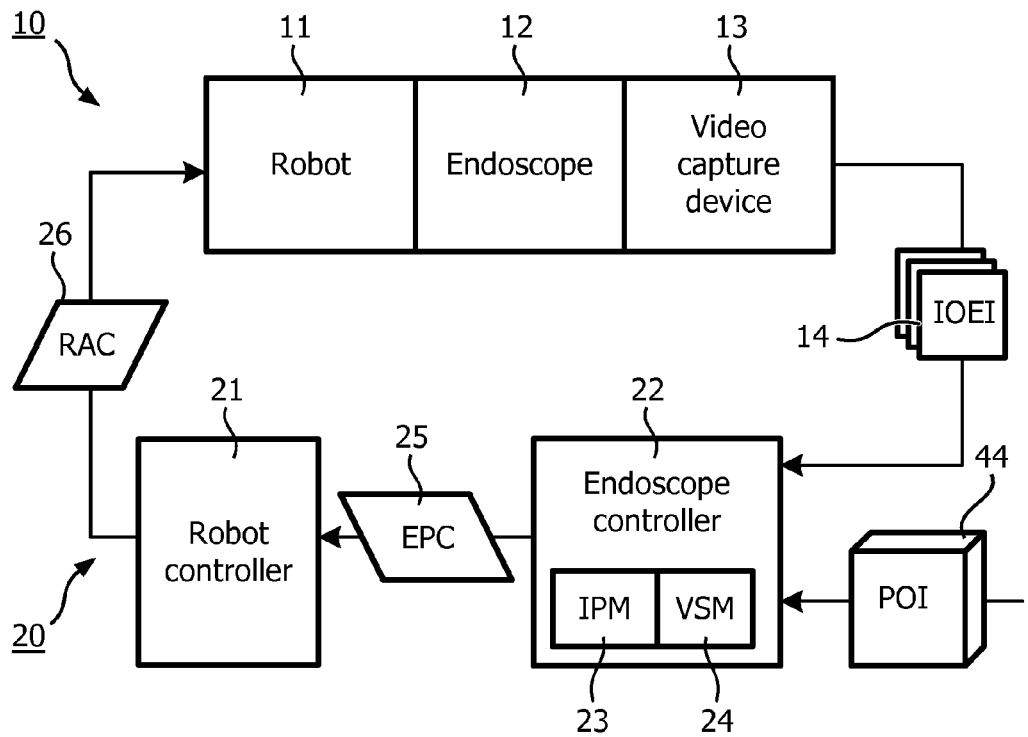
FIG. 1 illustrates an exemplary embodiment of a robotic guiding system in accordance with the present invention.

As shown in FIG. 1, a robotic guiding system employs a robot unit 10 and a control unit 20 for any endoscopic procedure involving an endoscopic imaging of a blood vessel tree having one or more furcations (i.e., branches). Examples of such endoscopic procedures include, but are not limited to, minimally invasive cardiac surgery (e.g., coronary artery bypass grafting or mitral valve replacement).

Robot unit 10 includes a robot 11, an endoscope 12 rigidly attached to robot 11 and a video capture device 13 attached to the endoscope 12.

Robot 11 is broadly defined herein as any robotic device structurally configured with motorized control of one or more joints for maneuvering an end-effector as desired for the particular endoscopic procedure. In practice, robot 11 may have four (4) degrees-of-freedom, such as, for example, a serial robot having joints serially connected with rigid segments, a parallel robot having joints and rigid segments mounted in parallel order (e.g., a Stewart platform known in the art) or any hybrid combination of serial and parallel kinematics.

Endoscope 12 is broadly defined herein as any device structurally configured with ability to image from inside a body. Examples of endoscope 12 for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, and miniaturized (e.g. CCD based) imaging systems.

In practice, endoscope 12 is mounted to the end-effector of robot 11. A pose of the end-effector of robot 11 is a position and an orientation of the end-effector within a coordinate system of robot 11 actuators. With endoscope 12 mounted to the end-effector of robot 11, any given pose of the field-of-view of endoscope 12 within an anatomical region corresponds to a distinct pose of the end-effector of robot 11 within the robotic coordinate system. Consequently, each individual endoscopic image of a blood vessel tree generated by endoscope 12 may be linked to a corresponding pose of endoscope 12 within the anatomical region.

Video capture device 13 is broadly defined herein as any device structurally configured with a capability to convert an intra-operative endoscopic video signal from endoscope 12 into a computer readable temporal sequence of intra-operative endoscopic image ("IOEI") 14. In practice, video capture device 13 may employ a frame grabber of any type for capturing individual digital still frames from the intra-operative endoscopic video signal.

Still referring to FIG. 1, control unit 20 includes a robot controller 21 and an endoscope controller 22.

Robot controller 21 is broadly defined herein as any controller structurally configured to provide one or more robot actuator commands ("RAC") 26 to robot 11 for controlling a pose of the end-effector of robot 11 as desired for the endoscopic procedure. More particularly, robot controller 21 converts endoscope position commands ("EPC") 25 from endoscope controller 22 into robot actuator commands 26. For example, endoscope position commands 25 may indicate an endoscopic path leading to desired 3D position of a field-of-view of endoscope 12 within an anatomical region whereby robot controller 21 converts command 25 into commands 26 including an actuation current for each motor of robot 11 as needed to move endoscope 12 to the desired 3D position.

Figure 2:
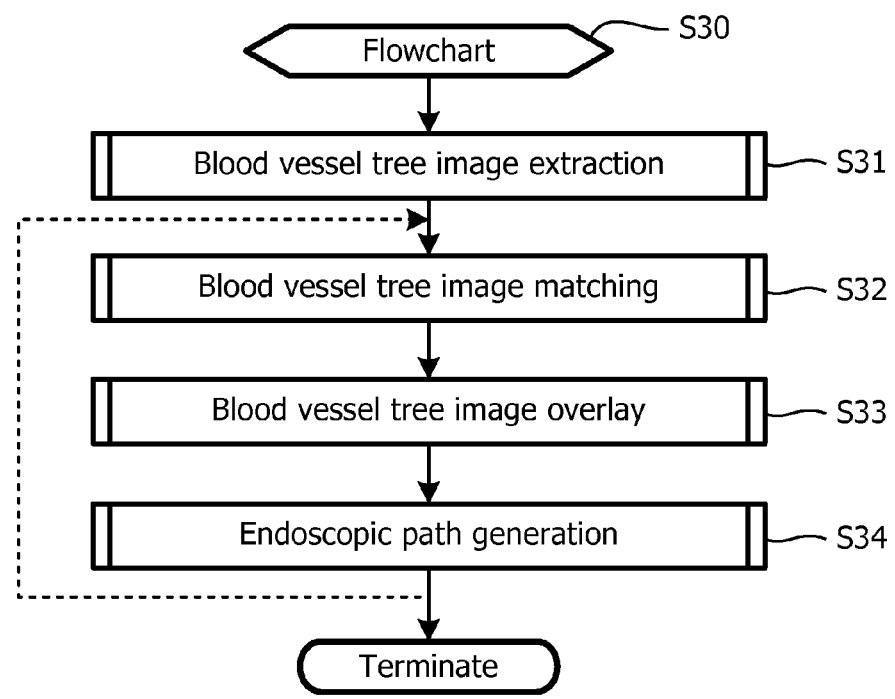
FIG. 2 illustrates a flowchart representative of an exemplary embodiment of a robotic guidance method in accordance with the present invention.

Endoscope controller 22 is broadly defined herein as any controller structurally configured for implementing a robotic guidance method in accordance with the present invention and exemplary shown in FIG. 2. To this end, endoscope controller 22 may incorporate an image processing module ("IPM") 23, which is broadly defined herein as any module structurally configured for executing an anatomical object image registration of the present invention. In particular, a blood vessel tree image registration as exemplarily implemented by stages S32 and S33 of flowchart 30 shown in FIG. 2. Endoscope controller 22 may further incorporate a visual servo module ("VSM") 24, which is broadly defined herein as any module structurally configured for generating endoscope position commands 25 indicating an endoscopic path leading to desired 3D position of a field-of-view of endoscope 12 within an anatomical region. In particular, endoscope position commands 25 are derived from the blood vessel tree image registration as exemplarily implemented by a stage S34 of flowchart 30 shown in FIG. 2.

A description of flowchart 30 will now be provided herein to facilitate a further understanding of endoscope controller 22.

Figure 3:
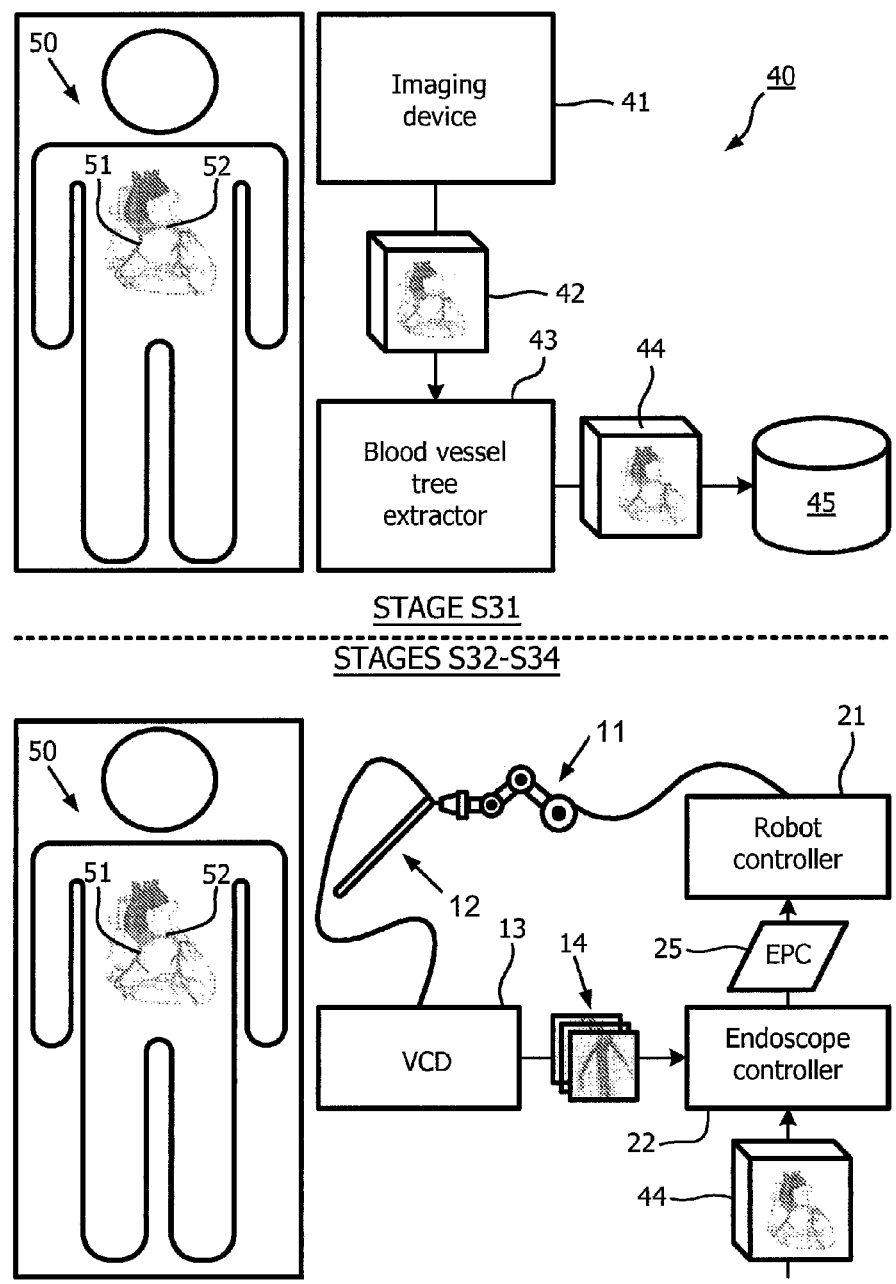
FIG. 3 illustrates an exemplary surgical implementation of the flowchart shown in FIG. 2

Referring to FIG. 2, a stage S31 of flowchart 30 encompasses an extraction of a geometrical representation of a blood vessel tree from a pre-operative 3D image. For example, as shown in FIG. 3, a 3D imaging device (e.g., a CT device, an X-ray device, or a MRI device) is operated to generate a pre-operative 3D image 42 of a chest region of a patient 50 illustrating left and right coronary arteries 51 and 52 of patient 50. Thereafter, a blood vessel tree extractor 43 is operated to extract a geometrical representation 44 of a coronary arterial tree from image 42, which may be stored in a database 45. In practice, a Brilliance iCT scanner sold by Philips may be used to generate image 42 and to extract a 3D dataset of the coronary arterial tree from image 42.

Referring back to FIG. 2, a stage S32 of flowchart 30 encompasses image processing module 23 matching the graphical representation of one or more intra-operative endoscopic images 14 (FIG. 1) of the blood vessel tree to a graphical representation of pre-operative 3D image 44 (FIG. 1) of the blood vessel tree. For example, as shown in FIG. 3, endoscope 12 generates an intra-operative endoscopy video of a chest region of patient 50 that is captured by video capture device 13 and converted into intra-operative endoscopic images 14 whereby image processing module 23 of endoscope controller 22 matches a graphical representation of the intra-operative endoscopic image(s) 14 of the coronary arterial tree to a graphical representation of pre-operative 3D image 44 of the coronary arterial tree. In one exemplary embodiment, image processing module 23 executes a blood vessel tree image matching method of the present invention as exemplarily represented by a flowchart 60 shown in FIG. 4, which will be described herein in the context of the blood vessel tree being a coronary arterial tree.

Figure 4:
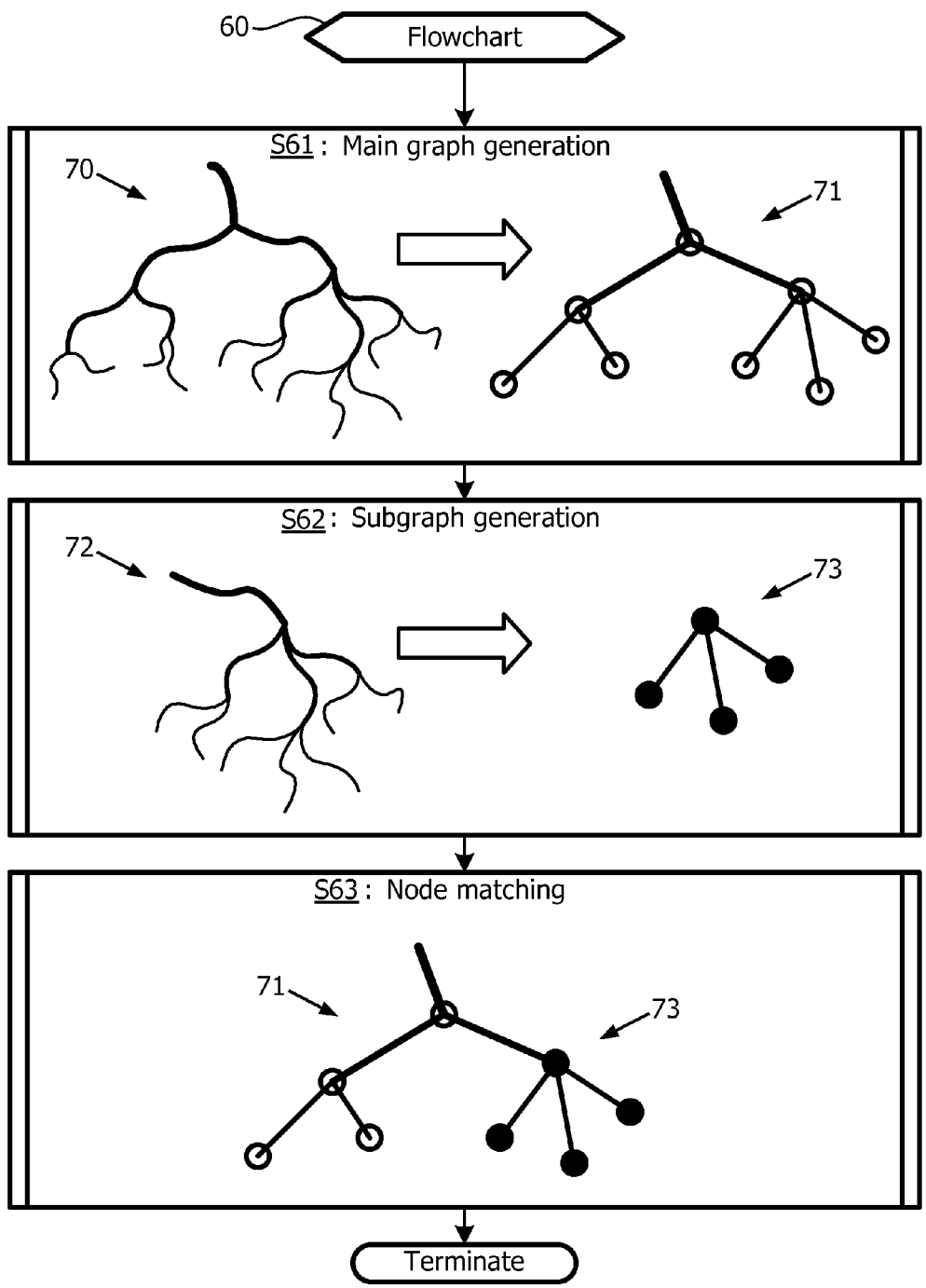
FIG. 4 illustrates a flowchart representative of an exemplary embodiment of a graph matching method in accordance with the present invention.

Referring to FIG. 4, a stage S61 of flowchart 60 encompasses image processing module 23 generating a coronary arterial tree main graph from a geometrical representation of the coronary arterial tree in accordance with any representation method known in the art. For example, as shown in stage S61, a geometrical representation 70 of a coronary arterial tree is converted into a main graph 71 having nodes represented of each furcation (e.g., a bifurcation or trifurcation) of coronary arterial tree geometrical representation 70 and further having branch connections between nodes. Stage S61 may be performed pre-operatively (e.g., days before the endoscopic surgery or any time prior to an introduction of endoscope 12 within patient 50), or intra-operatively by means of a C-arm angiography or other suitable system.

A stage S62 of flowchart 60 encompasses image processing module 23 generating a coronary arterial tree subgraph from a portion of a coronary arterial tree visible in an intra-operative endoscopic image 14 in accordance with any graphical representation method known in the art. Specifically, endoscope 12 is introduced into patient 50 whereby image processing module 23 performs a detection of a coronary arterial structure within the intra-operative endoscopic image 14. In practice, some arterial structures may be visible while other arterial structures may be hidden by a layer of fatty tissue. As such, image processing module 23 may implement an automatic detection of visible coronary arterial structure(s) by known image processing operations (e.g., threshold detection by the distinct red color of the visible coronary arterial structure(s)), or a surgeon may manually use an input device to outline the visible coronary arterial structure(s) on the computer display. Upon a detection of the arterial structure(s), image processing module 23 generates the coronary arterial tree graph in a similar manner to the generation of the coronary arterial tree main graph. For example, as shown in stage S62, a geometrical representation 72 of coronary arterial structure(s) is converted into a graph 73 having nodes represented of each furcation (e.g., a bifurcation or trifurcation) of coronary arterial tree geometrical representation 72 and further having branch connections between nodes. Since both trees are coming from the same person, it is understood that the graph derived from endoscopy images is a subgraph of the graph derived from 3D images.

A stage S63 of flowchart 60 encompasses image processing module 23 matching the subgraph to the maingraph in accordance with any known graph matching methods (e.g., maximum common subgraph or McGregor common subgraph). For example, as shown in stage S63, the nodes of subgraph 73 are matched to a subset of nodes of main graph 71.

In practice, subgraph 73 may only be partially detected within intra-operative endoscopic image 14 or some nodes/connections of subgraph 73 may be missing from intra-operative endoscopic image 14. To improve upon the matching accuracy of stage S62, an additional ordering of main graph 71 and subgraph 73 may be implemented.

Figure 5:
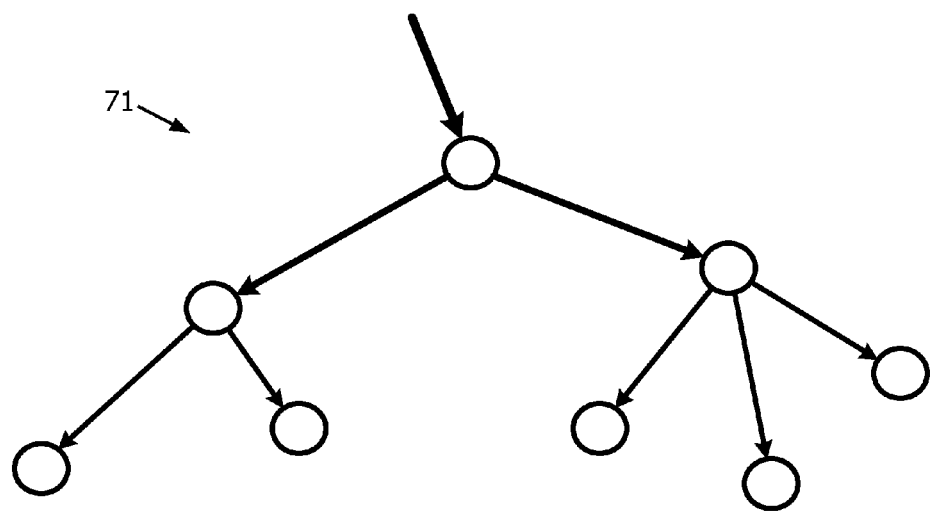
FIGS. 5 and 6 illustrate an exemplary ordering of main graphs of a blood vessel tree in accordance with the present invention.

In one embodiment, a vertical node ordering of main graph 71 is implemented based on a known orientation of patient 50 during the image scanning of stage S61. Specifically, the main graph nodes may be directionally linked to preserve a top-bottom order as exemplarily shown in FIG. 5 via the solid arrows. For subgraph 73, the orientation of patient 50 relative to endoscope 12 may not be known. However, knowing that branches of the coronary arterial tree reduce in diameter as they expand top-bottom, then varying arterial sizes of the arterial branches in intra-operative endoscopic image 14 may indicate orientation.

Figure 6:
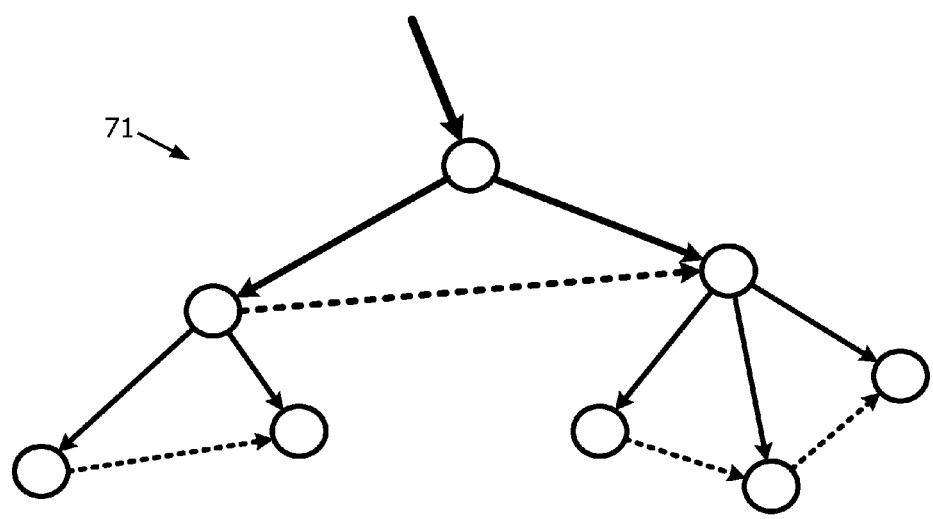

In another embodiment, a horizontal node ordering of main graph 70 may be implemented based on the known orientation of patient 50 during the image scanning of stage S61. Specifically, the main graph nodes may be directionally linked to preserve a left-right node order as exemplarily shown in FIG. 6 via the dashed arrows. For subgraph 73, with the orientation of patient 50 to endoscope 12 more than likely being unknown, the horizontal node order of subgraph 73 may be set by the operating surgeon or an assistant via a graphical user interface.

While the use of ordering may decrease the time for matching the graphs and reduce the number of possible matches, theoretically multiple matches between the graphs may still be obtained by the matching algorithm. Such a case of multiple matches is addressed during a stage S33 of flowchart 30.

Referring again to FIG. 2, based on the matching of the graphs, a stage S33 of flowchart encompasses an overlay of the geometrical representation of pre-operative 3D image 44 (FIG. 1) of the blood vessel tree on the intra-operative endoscopic image 14 of the blood vessel tree. This is done by using the geometrical representation uniquely associated to the maingraph. Thus, the entire geometry may be directly translated to intra-operative endoscopic image 14 using a perspective transformation. The perspective transformation may be detected from intra-operative endoscopic image 14 and nodes in pre-operative 3D image 44 using matching algorithms known in art, such as, of example, homography matching.

Figure 7:
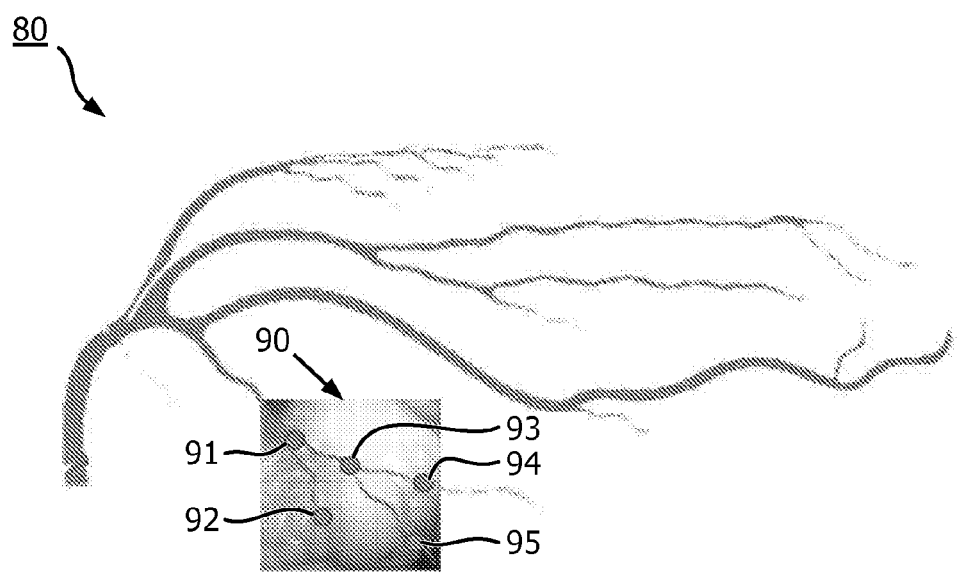
FIG. 7 illustrates an exemplary overlay of geometrical representation on an endoscopic image accordance with the present invention.

For example, FIG. 7 illustrates a geometrical representation 80 of a coronary arterial tree having nodes matched to nodes 91-95 with an intra-operative endoscopic image 90. The distance between each node pair among nodes 91-95 may be used to determine a scaling factor for geometrical representation 80 to thereby enable geometrical representation 80 to overlay intra-operative endoscopic image 90 as shown.

In practice, if the graph matching of stage S32 (FIG. 2) yields multiple results, then all possible overlays may be displayed to the surgeon whereby the surgeon may select the matching result the surgeon believes is the most likely match via a graphical user interface. Given that the surgeon knows the position of endoscope 12 relative to at least some structures in intra-operative endoscopic image 14, the selection may be relatively straightforward.

Figure 8:
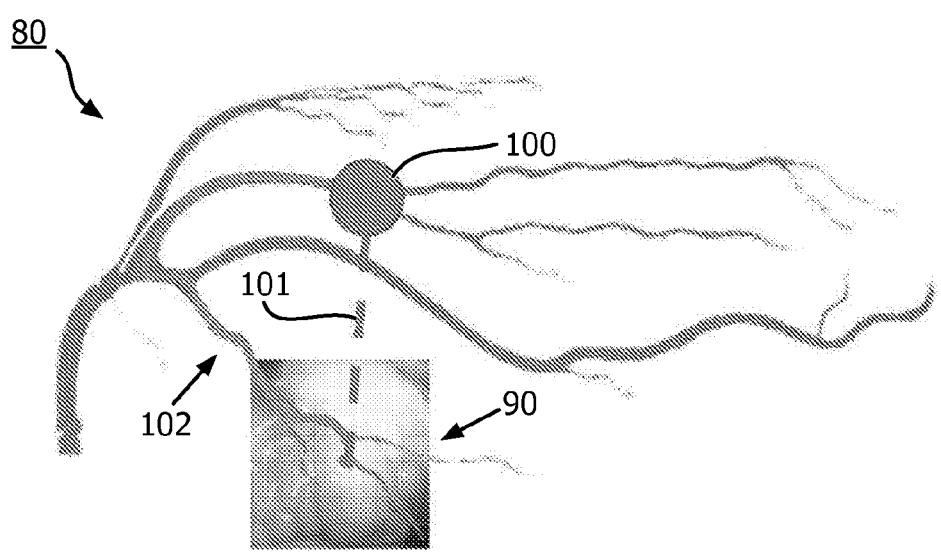
FIG. 8 illustrates an exemplary robot paths within the overlay shown in FIG. 7 in accordance with the present invention.

Referring back to FIG. 2, a stage S34 of flowchart 30 encompasses visual servo module 32 generates an endoscopic path within the overlay of the geometrical representation of pre-operative 3D image 44 (FIG. 1) of the blood vessel tree on intra-operative endoscopic image 14 (FIG. 1) of the blood vessel tree. Based on the endoscopic path, visual servo module 32 generates endoscope position command's 25 to robot controller 21 to thereby guide endoscope 12 (FIG. 1) along the endoscopic path to a desired position within the anatomical region. Specifically, once the exact overlay is found, robot 11 may be commanded to guide endoscope 12 to positions the surgeon selects on pre-operative 3D image 44. The surgeon or the assistant may select a point of blood vessel tree, and robot 11 may guide endoscope 12 towards that desired position along any suitable path. For example, as shown in FIG. 9, FIG. 8, robot 11 may move endoscope 12 along a shortest path 101 to a desired position 100 or along an coronary arterial path 102 to desired position 100. Coronary arterial path 102 is the preferred embodiment, because coronary arterial path 102 allows the surgeon to observe visible arteries as robot 11 moves endoscope 12. In addition, it might help the surgeon to decide if the matching was successful. Coronary arterial path 102 may be defined using methods known in art (e.g., Dijkstra shortest path algorithm).

In practice, the movement of robot 11 may be commanded using uncalibrated visual servoing with remote center of motion, and the field of view of endoscope 12 may be extended to enable a larger subgraph during matching stage S32.

Referring back to FIG. 2, stages S32-S34 may either be executed one time, or on a periodical basis until such time robot 11 has moved endoscope 12 to the desired position within the anatomical region, or multiple times as dictated by the surgeon.

In practice, modules 23 and 24 (FIG. 1) may be implemented by hardware, software and/or firmware integrated within endoscope controller 22 as shown.

From the description of FIGS. 1-8 herein, those having ordinary skill in the art will appreciate the numerous benefits of the present invention including, but not limited to, an application of the present invention to any type of endoscopy surgery performed on any type of blood vessels.

Although the present invention has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present invention. Accordingly, the present invention expressly encompasses such modification, alterations and enhancements within the scope hereof.

The invention claimed is:

1. A robot guiding system, comprising:
an endoscope including an endoscope camera configured to generate an intra-operative endoscopic image of an exterior of a subregion of a blood vessel tree within an anatomical region;
a robot configured to move the endoscope within the anatomical region exterior to blood vessels of the blood vessel tree;
an endoscope controller configured to:
generate an endoscopic path exterior to the blood vessels within the anatomical region, wherein the endoscopic path follows vessels of the blood vessel tree and the endoscopic path is derived from matching a graphical representation of the intra-operative endoscopic image of the subregion of the blood vessel tree to a graphical representation of a pre-operative three-dimensional image of the blood vessel tree,
overlay the geometrical representation of the pre-operative three-dimensional image of the exterior of the blood vessel tree onto the intra-operative endoscopic image of the subregion of the blood vessel tree corresponding to the subgraph in accordance with the matching of the graphical representation of the intra-operative endoscopic image of the blood vessel tree to the graphical representation of the pre-operative three-dimensional image of the blood vessel tree, and
generate the endoscopic path within the geometrical representation of the pre-operative three-dimensional image of the exterior of the blood vessel tree overlaid onto the intra-operative endoscopic image of the corresponding portion of the blood vessel tree; and
a robot controller configured to command the robot to move the endoscope within the anatomical region exterior to the blood vessels in accordance with the endoscopic path;
wherein the endoscopic controller is further configured to update the generating of the endoscopic path, the overlay, and the generating of the endoscopic path within the geometrical representation as the robot moves the endoscope within the anatomical region exterior to blood vessels of the blood vessel tree.

2. The robot guiding system of claim 1, wherein the matching of the graphical representation of the intra-operative endoscopic image of the blood vessel tree to the graphical representation of the pre-operative three-dimensional image of the blood vessel tree includes:
generating a main graph derived from the geometrical representation of the pre-operative three-dimensional image of the blood vessel tree;
generating a subgraph derived from a geometrical representation of the intra-operative endoscopic image of the subregion of the blood vessel tree; and
matching the subgraph to the main graph.

3. The robot guiding system of claim 2, wherein the matching of the subgraph to the main graph includes matching nodes of the subgraph to nodes of subregions of the main graph to locate one or more candidate subregions of the main graph corresponding to the subgraph; and
wherein one of the plurality of the candidate subregions located from the matching is selected as a match of the subgraph to the main graph.

4. The robot guiding system of claim 1, wherein the blood vessel tree is a coronary artery tree.

5. A robot guiding system comprising:
an endoscope including an endoscope camera configured to generate an intra-operative endoscopic image of an exterior of a subregion of a blood vessel tree within an anatomical region;
a robot configured to move the endoscope within the anatomical region exterior to blood vessels of the blood vessel tree;
an endoscope controller configured to generate an endoscopic path exterior to the blood vessels within the anatomical region, wherein the endoscopic path is derived from matching a graphical representation of the intra-operative endoscopic image of the subregion of the blood vessel tree to a graphical representation of a pre-operative three-dimensional image of the blood vessel tree, wherein the matching of the graphical representation of the intra-operative endoscopic image of the blood vessel tree to the graphical representation of the pre-operative three-dimensional image of the blood vessel tree includes:
  generating a main graph derived from the geometrical representation of the pre-operative three-dimensional image of the blood vessel tree, wherein the main graph includes a main set of nodes representative of each furcation of the blood vessel tree within the pre-operative three-dimensional image of the blood vessel tree,
  generating a subgraph derived from a geometrical representation of the intra-operative endoscopic image of the subregion of the blood vessel tree, wherein the subgraph includes a subset of the main set of nodes, the subset of nodes being representative of each furcation of the blood vessel tree within the intra-operative endoscopic image of the blood vessel tree, and
  matching the subgraph to the main graph, wherein the matching of the subgraph to the main graph includes establishing at least one of a vertical ordering and a horizontal ordering of the nodes in the main graph;
a robot controller configured to command the robot to move the endoscope within the anatomical region exterior to the blood vessels in accordance with the endoscopic path.

6. A robot guiding method, comprising:
with an endoscope mounted camera, generating an intra-operative endoscopic image of a subregion of a blood vessel tree visible to the endoscope within an anatomical region;
with a processor, matching a graphical representation of the intra-operative endoscopic image of the subregion of the blood vessel tree to a graphical representation of a pre-operative three-dimensional image of the blood vessel tree, wherein the matching of the graphical representation of the intra-operative endoscopic image of the subregion of the blood vessel tree to the graphical representation of the pre-operative three-dimensional image of the blood vessel tree includes:
  with the processor, generating a main graph derived from a geometrical representation of the pre-operative three-dimensional image of the blood vessel tree;
  with the processor, generating a subgraph derived from a geometrical representation of the intra-operative endoscopic image of the subregion of the blood vessel tree; and
  with the processor, matching the subgraph to subregions of the main graph to locate a main graph subregion corresponding to the subgraph;
with the processor, generating a path within the anatomical region that follows vessels of the blood vessel tree from a first location in the subregion of the blood vessel tree visible to the endoscope camera to a second location in the pre-operative three-dimensional image of the blood vessel tree;
with a robot controller, commanding a robot to move the endoscope within the anatomical region in accordance with the path to a location in the anatomical region corresponding to the second location;
with the processor, controlling a display device to overlay the geometrical representation of the pre-operative three-dimensional image of the blood vessel tree onto the intra-operative endoscopic image of the subregion of the blood vessel tree in accordance with the matching of the graphical representation of the intra-operative endoscopic image of the subregion of the blood vessel tree to the graphical representation of the pre-operative three-dimensional image of the blood vessel tree; and
with the processor, updating the matching and controlling the display device to update the overlay of the geometrical representation of the pre-operative three-dimensional image of the blood vessel tree onto the intra-operative endoscopic image of the subregion of the blood vessel tree as the robot moves the endoscope within the anatomical region in accordance with the path.

7. The robot guiding method of claim 6, wherein the main graph includes a main set of nodes representative of each furcation of the blood vessel tree within the pre-operative three-dimensional image of the blood vessel tree; and
  wherein the subgraph includes a subset of the main set of nodes, the subset of nodes being representative of each furcation of the blood vessel tree within the intra-operative endoscopic image of the subregion of the blood vessel tree visible to the endoscope camera.

8. A robot guiding system, comprising:
an endoscope including a surgical element and an optical camera configured to generate an intra-operative endoscope image data;
a robot controller configured to control a robot to move the endoscope through an anatomical region of a patient;
a display device; and
one or more processors configured to:
  generate a preoperative 3D image of a blood vessel tree from image data generated by a 3D diagnostic imaging system,
  generate an intra-operative endoscope image of a subregion of the blood vessel tree visible to the endoscope camera,
  match the intra-operative endoscope image and a corresponding subregion of the pre-operative 3D blood vessel tree image,
  overlay the matched intra-operative endoscope image and the pre-operative 3D blood vessel tree image,
  control the display device to display the overlaid matched intra-operative endoscope and pre-operative 3D blood vessel tree images and a path from the a selected location in the intra-operative endoscope image to a selected surgical site in the pre-operative 3D blood vessel tree image, wherein the path follows vessels of the blood vessel tree, and
  update the matching, overlaying, and displaying as the endoscope is moved along the path to provide a visual confirmation that the matching was successful.

9. The robot guiding system of claim 8, wherein the processor is further configured to:
  process the pre-operative 3D blood vessel image to generate a main graph in which the blood vessel tree is depicted by nodes representing furcations of the blood vessel tree interconnected by lines depicting vessels of the blood vessel tree;
  process the intra-operative endoscope image to generate a subgraph in which furcations of blood vessels are represented by nodes interconnected by lines representing vessels;
  wherein the matching includes matching the subgraph with the main graph to find the subregion of the blood vessel tree that corresponds to the subregion of the blood vessel tree visible in the intra-operative endoscope image.

10. A robot guiding system comprising:
an endoscope including a surgical element and an optical camera configured to generate an intra-operative endoscope image data;
a robot controller configured to control a robot to move the endoscope through an anatomical region of a patient;
a display device; and
one or more processors configured to:
  generate a preoperative 3D image of a blood vessel tree from image data generated by a 3D diagnostic imaging system,
  generate an intra-operative endoscope image of a subregion of the blood vessel tree visible to the endoscope camera,
  match the intra-operative endoscope image and a corresponding subregion of the pre-operative 3D blood vessel tree image,
  overlay the matched intra-operative endoscope image and the pre-operative 3D blood vessel tree image,
  control the display device to display the overlaid matched intra-operative endoscope and pre-operative 3D blood vessel tree images and a path from the a selected location in the intra-operative endoscope image to a selected surgical site in the pre-operative 3D blood vessel tree image,
  process the pre-operative 3D blood vessel image to generate a main graph in which the blood vessel tree is depicted by nodes representing furcations of the blood vessel tree interconnected by lines depicting vessels of the blood vessel tree; and
  process the intra-operative endoscope image to generate a subgraph in which furcations of blood vessels are represented by nodes interconnected by lines representing vessels;
wherein the matching includes matching the subgraph with the main graph including establishing at least one of a vertical ordering and a horizontal ordering of the nodes in the main graph to find the subregion of the blood vessel tree that corresponds to the subregion of the blood vessel tree visible in the intra-operative endoscope image.

11. A robot guiding system comprising:
an endoscope including a surgical element and an optical camera configured to generate an intra-operative endoscope image data;
a robot controller configured to control a robot to move the endoscope through an anatomical region of a patient;
a display device; and
one or more processors configured to:
  generate a preoperative 3D image of a blood vessel tree from image data generated by a 3D diagnostic imaging system,
  process the pre-operative 3D blood vessel image to generate a main graph in which the blood vessel tree is depicted by nodes representing furcations of the blood vessel tree interconnected by lines depicting vessels of the blood vessel tree;
  generate an intra-operative endoscope image of a subregion of the blood vessel tree visible to the endoscope camera,
  process the intra-operative endoscope image to generate a subgraph in which furcations of blood vessels are represented by nodes interconnected by lines representing vessels;
  match the intra-operative endoscope image and a corresponding subregion of the pre-operative 3D blood vessel tree image, wherein the matching of the subgraph to the main graph includes:
    matching the nodes of the subgraph to the nodes of the main graph to generate a plurality of candidate matches; and
    wherein the one or more processors are further configured to display the candidate matches for user selection;
  overlay the matched intra-operative endoscope image and the pre-operative 3D blood vessel tree image,
  control the display device to display the overlaid matched intra-operative endoscope and pre-operative 3D blood vessel tree images and a path from a selected location in the intra-operative endoscope image to a selected surgical site in the pre-operative 3D blood vessel tree image.

12. A robot guiding system comprising:
an endoscope including a surgical element and an optical camera configured to generate an intra-operative endoscope image data;
a robot controller configured to control a robot to move the endoscope through an anatomical region of a patient;
a display device; and
one or more processors configured to:
  generate a preoperative 3D image of a blood vessel tree from image data generated by a 3D diagnostic imaging system, wherein the blood vessel tree is a coronary artery tree,
  generate an intra-operative endoscope image of a subregion of the blood vessel tree visible to the endoscope camera,
  match the intra-operative endoscope image and a corresponding subregion of the pre-operative 3D blood vessel tree image,
  overlay the matched intra-operative endoscope image and the pre-operative 3D blood vessel tree image,
  control the display device to display the overlaid matched intra-operative endoscope and pre-operative 3D blood vessel tree images and a path from the a selected location in the intra-operative endoscope image to a selected surgical site in the pre-operative 3D blood vessel tree image.

* * * * *